(12) United States Patent
Hara et al.

(10) Patent No.: US 7,971,634 B2
(45) Date of Patent: Jul. 5, 2011

(54) AIR CONDITIONER AND ANTIBACTERIAL CASE

(75) Inventors: Shinichi Hara, Konan-Machi (JP); Yutaka Teruya, Konan-Machi (JP); Yuusuke Takahashi, Konan-Machi (JP)

(73) Assignee: Valeo Climatisation, La Verriere (FR)

( * ) Notice: Subject to any disclaimer, the term of this patent is extended or adjusted under 35 U.S.C. 154(b) by 1160 days.

(21) Appl. No.: 10/564,602

(22) PCT Filed: Jul. 23, 2004

(86) PCT No.: PCT/IB2004/002655
§ 371 (c)(1),
(2), (4) Date: Jan. 12, 2006

(87) PCT Pub. No.: WO2005/009493
PCT Pub. Date: Feb. 3, 2005

(65) Prior Publication Data
US 2006/0225869 A1    Oct. 12, 2006

(30) Foreign Application Priority Data
Jul. 24, 2003    (JP) .................................. 2003-279129

(51) Int. Cl.
*F28F 19/00*    (2006.01)
*A62B 7/08*    (2006.01)

(52) U.S. Cl. ..................................... 165/134.1; 165/119

(58) Field of Classification Search .................. 165/119, 165/134.1, 79; 96/222; 454/156; 422/120; 206/335, 484.1
See application file for complete search history.

(56) References Cited

U.S. PATENT DOCUMENTS

| | | | | |
|---|---|---|---|---|
| 4,961,493 | A * | 10/1990 | Kaihatsu | 206/5 |
| 5,458,244 | A * | 10/1995 | Emori | 206/527 |
| 5,759,844 | A * | 6/1998 | Hiraki et al. | 435/259 |
| 6,487,868 | B2 * | 12/2002 | Sato et al. | 62/176.1 |

FOREIGN PATENT DOCUMENTS

| | | | | |
|---|---|---|---|---|
| JP | 10230011 | A | * | 9/1998 |
| JP | 10315757 | A | * | 12/1998 |
| JP | 11201624 | A | * | 7/1999 |
| JP | 2000088270 | A | * | 3/2000 |
| JP | 2001231721 | A | * | 8/2001 |
| JP | 2003246215 | A | * | 9/2003 |
| WO | WO 0106876 | A1 | * | 2/2001 |

* cited by examiner

*Primary Examiner* — Tho v Duong
(74) *Attorney, Agent, or Firm* — Howard & Howard Attorneys PLLC

(57) ABSTRACT

Air conditioner pertaining to the present invention in which a synthetic polymer case, in which an antibacterial agent impregnated in a medium such as a porous body or water-absorbing polymer is sealed, is arranged in the upstream airflow side and/or downstream airflow side of an evaporator, which air conditioner is characterized in that the thickness of the wall of the case is formed to allow gas permeation of the antibacterial agent, and in that the thickness of the wall on the downstream airflow side is less than the thickness of the wall on the upstream airflow side.

10 Claims, 8 Drawing Sheets

AIR CONDITIONER AND ANTIBACTERIAL CASE

CROSS-REFERENCE TO RELATED APPLICATIONS

This application claims the benefit of U.S. Provisional Application No. 60/443,660, filed on Jan. 30, 2003. The disclosure of the above application is incorporated herein by reference.

BACKGROUND OF THE INVENTION

1. Field of the Invention

The present invention relates to an air conditioner that comprises a function that prevents the propagation of microorganisms in the evaporator and in the environs thereof or, more particularly, to a vehicle air conditioner and an antibacterial case arranged in the air passageway thereof.

2. Description of the Related Art

The activity of microorganisms such as bacteria that propagate in air conditioners is recognized as a major cause of the generation of unpleasant odours from car air conditioners. Environments such as this in which bacteria propagation is liable to occur are created in air conditioners due to the water that condenses as dew that is generated by the evaporator core. Antibacterial treatments and drying of the units have been considered as measures for preventing microorganism propagation.

Although a significant number of methods involving the compounding of antibacterial agents in the resin of the air conditioner have been attempted, there is a problem inherent to these methods in that the effect of the antibacterial agent is lost when dust accumulates on the antibacterial agent. Accordingly, the use of a volatile antibacterial agent has been proposed as a measure to deal with this (for example Japanese Unexamined Patent Application 11-211126, Japanese Unexamined Patent Application 11-211126 and Japanese Patent 6-78821).

Although the techniques used in the prior art have involved the placing of the volatile antibacterial agent within the air conditioner, these techniques gave no consideration to the fact that, when a volatile antibacterial agent is provided in a vehicle air conditioner, because temperatures within the air conditioner reach temperature of up to 50° C. in the summer months, the level of volatilization of the antibacterial agent increases and the lifespan thereof is shortened.

Thereupon, the focus of research changed to the development of an antibacterial agent case where it became known that, because of the gas-permeable property of polypropylene, if isocyanates and, in particular, ally isothiocyanate (AIT), was employed as the antibacterial agent, the reliance on temperature and the reliance on the quantity of blown air within the air passageway with respect to the level of volatilization could be improved by controlling the thickness of the wall.

SUMMARY OF THE INVENTION AND ADVANTAGES

An objective of the present invention, which focuses on the premise that the airflow formed in the air passageway of the air conditioner is one-directional and that this airflow strikes the upstream airflow side case wall surface, is to slowly disseminate the antibacterial agent without affect by the airflow. That is to say, the antibacterial agent from the upstream airflow side case wall surface which the airflow is liable to strike is liable to volatilize and, accordingly, the antibacterial agent is used in large amounts, it has a shortened lifespan and, moreover, the cycle for replacing the antibacterial agent is shortened. Accordingly, the objective is to reduce the likelihood of the airflow affecting the antibacterial agent as it is slowly disseminated from the case.

The tank part of the evaporator is provided close to the wall surface of the air passageway and airflow in the vicinity of the tank part is obstructed. An objective of the present invention is, by utilizing the fact that an airflow is unlikely to be generated near the tank part, to prevent the volatilization of the antibacterial agent caused by a received flow and, furthermore, when an antibacterial agent case is to be newly arranged, to arrange the case in a position that satisfies the need for there to be no additional airflow obstruction generated.

An objective of the present invention is that it be designed in such a way that, simultaneously with the implementation of the maintenance operation of the filter, the replacement of the antibacterial agent be able to be performed easily. Another objective thereof is to arrange the case in such a way that there is no obstruction to the airflow.

A further objective of the present invention is, where the antibacterial agent is arranged in the downstream side from the elevator, to provide another mode for the positional arrangement of the case that prevents volatilization of the antibacterial agent caused by a received flow.

Another objective of the present invention is to provide an antibacterial agent case in a shape that affords the slow dissemination of the antibacterial agent, and that prevents volatilization of the antibacterial agent caused by a received flow.

The inventors experimented with the antibacterial agent case shape and positional arrangement to develop an air conditioner that resolves the above-noted problems. That is to say, the air conditioner pertaining to the present invention, in an air conditioner that comprises, in an air passageway through which an airflow from an air intake port towards a clean air discharge port is formed, at the least, an air blower for generating airflow, an evaporator, and a synthetic polymer case, in which an antibacterial agent impregnated in a medium such as a porous body or water-absorbing polymer is sealed, arranged in the upstream airflow side and/or downstream airflow side of said evaporator, is characterized in that the thickness of the wall of the abovementioned case is formed to allow gas permeation of the antibacterial agent, and in that the thickness of the wall on the downstream airflow side is less than the thickness of the wall on the upstream airflow side.

In the air conditioner pertaining to the present invention, the abovementioned evaporator is preferably a single tank-type in which a tank is provided in one end or a double tank-type type in which tank parts are provided in both ends, and the abovementioned case is preferably arranged next to the abovementioned tank part. Here, it is preferable that the abovementioned case does not project from the abovementioned tank part with respect to the direction of airflow.

In the air conditioner pertaining to the present invention, it is preferable that the abovementioned case be detachably fixed to a filter frame arranged in the upstream airflow side of the abovementioned evaporator.

In the air conditioner pertaining to the present invention, in an air conditioner that comprises, in an air passageway through which an airflow from an air intake port towards a clean air discharge port is formed, at the least, an air blower for generating airflow, an evaporator of a single tank-type in which a tank is provided in one end or a double tank-type type in which tank parts are provided in both ends, and a synthetic polymer case, in which an antibacterial agent impregnated in a medium such as a porous body or water-absorbing polymer is sealed, arranged in the upstream airflow side and/or downstream airflow side of said evaporator, it is preferable that the abovementioned case be formed of a the thickness of the wall that allows gas permeation of the antibacterial agent, and that the thickness of the wall on the abovementioned elevator side be less than the thickness of the wall on the downstream airflow side. Here, it is preferable that the abovementioned case does not project from the abovementioned tank part with respect to the direction of airflow.

In the air conditioner pertaining to the present invention, it is preferable that the abovementioned case be formed from polypropylene, and that the abovementioned antibacterial agent be allyl isothiocyanate.

In the air conditioner pertaining to the present invention, it is preferable that the abovementioned case be formed by the assembly of a plurality of small cases detachably fixed to each other.

An antibacterial agent case pertaining to the present invention, which constitutes a synthetic polymer case in which an antibacterial agent impregnated in a medium such as a porous body or water-absorbing polymer is sealed, is characterized in that the thickness of one wall of said case is formed to be thinner than the wall opposing said wall.

It is preferable that the antibacterial agent case pertaining to the present invention be formed from polypropylene, and that the abovementioned antibacterial agent be allyl isothiocyanate.

Furthermore, in the antibacterial agent case pertaining to the present invention, it is preferable that the abovementioned case be formed by the assembly of a plurality of small cases detachably fixed to each other.

In the present invention, improvements to the reliance on temperature dependency and the reliance on the quantity of blown air within the air passageway with respect to the level of volatilization are achieved by controlling the thickness of the wall of the antibacterial agent case. By thickening the wall of the upstream airflow side case wall surface which the airflow is liable to strike, imparting a directional characteristic to the slow dissemination of the antibacterial agent by reducing the thickness of the downstream side, and preventing the volatilization of the antibacterial agent caused by a received flow, the cycle for the replacement of the antibacterial agent can be lengthened.

By the juxtaposing of the case with the tank part and, preferably, juxtaposing the case in such a way that is does not project from the tank part of the evaporator with respect to the direction of airflow, the volatilization of the antibacterial agent caused by a received flow of airflow can be prevented, and increase in the obstruction of the airflow caused by the positioning of the case can be prevented.

Furthermore, in the present invention, simultaneously with the maintenance of the filter, the replacement of the antibacterial agent can be easily implemented.

Furthermore, in the present invention, in the case where the antibacterial agent case is arranged in the downstream side from the evaporator, by juxtaposing the case with the tank part and reducing thickness of the evaporator side case wall, the volatilization of the antibacterial agent caused by the received flow of airflow can be prevented and, in addition, the antibacterial agent can be volatilized in the direction of the evaporator where the propagation of the microorganisms occurs.

The antibacterial agent case of the present invention affords the slow dissemination of the antibacterial agent with directionality and prevents volatilization of the antibacterial agent caused by the received flow of airflow.

DETAILED DESCRIPTION OF THE INVENTION

Figure 1:
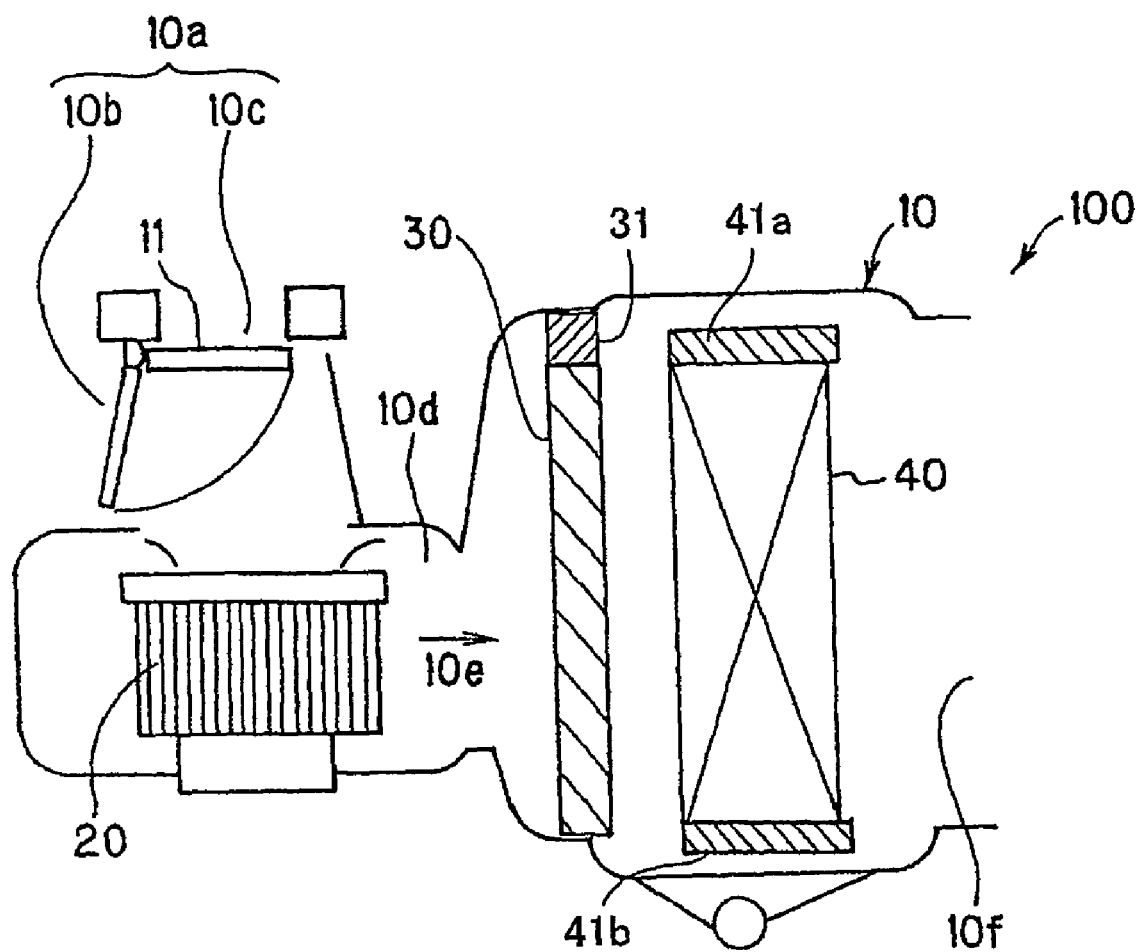
FIG. 1 shows a side-surface schematic view of an air passageway from an air intake port to an evaporator of the air conditioner pertaining to this embodiment when assembled in a vehicle.

Although a detailed description of the present invention is given below with reference to the embodiments thereof, the present invention is in no way to be interpreted as being limited to this description. FIG. 1 shows a side-surface schematic view of an air passageway from an air intake port to an evaporator of the air conditioner pertaining to this embodiment when assembled in a vehicle. The air conditioner 100 comprises an air conditioner main body 10 in which an air passageway is formed. An air suction port 10*a* configured from an interior air suction port 10*b* and exterior air suction port 10*c* which are opened and closed by a damper 11, and an air passageway 10*d* that has communication with the air suction port 10*a* and a clean air discharge port 10*f*, are provided in the air conditioner main body 10. A blower 20, which is an air blower, a filter unit 30 and an evaporator 40 are provided in the air passageway 10*d* in sequence from the upstream side. When the blower 20 is driven, air is drawn in from the side of the air suction port 10*a* that opens to the air passageway 10*d*. After this, the air passes through the filter unit 30 and is cooled by the evaporator 40 to form an airflow 10*e*. Following this, by way of an air mix door (not shown in the diagram) and a heater (not shown in the diagram) and so on, this air is blown into the vehicle interior.

Although, in FIG. 1, the blower 20, filter unit 30 and evaporator 40 are shown arranged in this sequence upstream of the airflow 10*e*, they may be arranged in the sequence of filter unit, evaporator and blower, or arranged in the sequence of filter unit, blower and evaporator.

The filter unit 30, which is provided to clean the air, constitutes either a single dust-collecting filter or a filter formed from the assembly of a dust-collecting filter and odour-removing filter which are assembled in a filter frame to which the filter end part is fixed in a way not to cover the filter surface. These filters are preferably produced in a pleated shape to maximize the filter surface area. In addition, where an odour-removing filter is provided, it is even more preferable that a photocatalyst be carried on the odour-removing filter and that the odour-removing component affixed to the odour-removing filter be decomposed using a UV-ray generating lamp. It should be noted that it is preferable that, in order for the filter frame to be detachably fixed to the air conditioner device 10, a latching hook (not shown in the diagram) be provided in the filter frame. As a result, the maintenance and replacement of the filters is simplified. It should be noted that the UV-ray generating lamp may either be supported by the air conditioner main body 10 without fixing to the filter frame, or it may be fixed to the filter frame. In addition, the filter frame may be partitioned into a lattice shape, and filters may be assembled in each of these partitioned frames.

In the air conditioner pertaining to this embodiment mode, a synthetic polymer case, in which an antibacterial agent impregnated in a medium such as a porous body or water-absorbing polymer is sealed, is arranged in the upstream airflow side or the downstream airflow side of the evaporator or in both the upstream airflow side and the downstream airflow side of the evaporator. The reason for the arrangement of the synthetic polymer case both forward and rear of the airflow of the evaporator is because an environment in which the microorganisms can easily propagate is generated in the evaporator due to water that condenses as dew, and the slow dissemination of the antibacterial agent prevents the propagation of microorganisms in the evaporator and the environs thereof.

Figure 2:
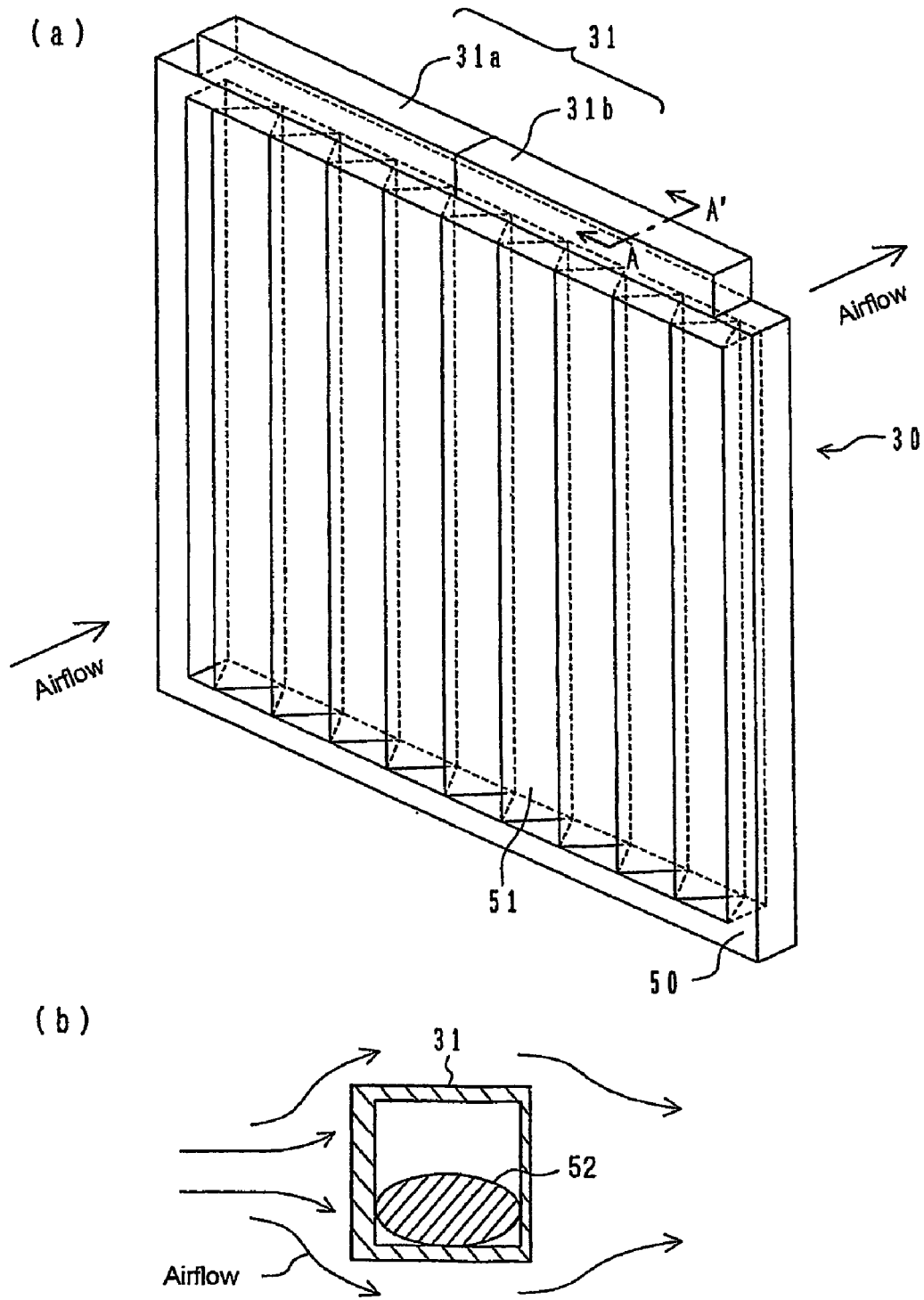
FIG. 2 is a type diagram of the filter unit and antibacterial agent case of FIG. 1, wherein (a) is a type diagram that shows the usage state thereof and (b) is a schematic view along the cross-section A-A' of the antibacterial agent case 31.
Figure 3:
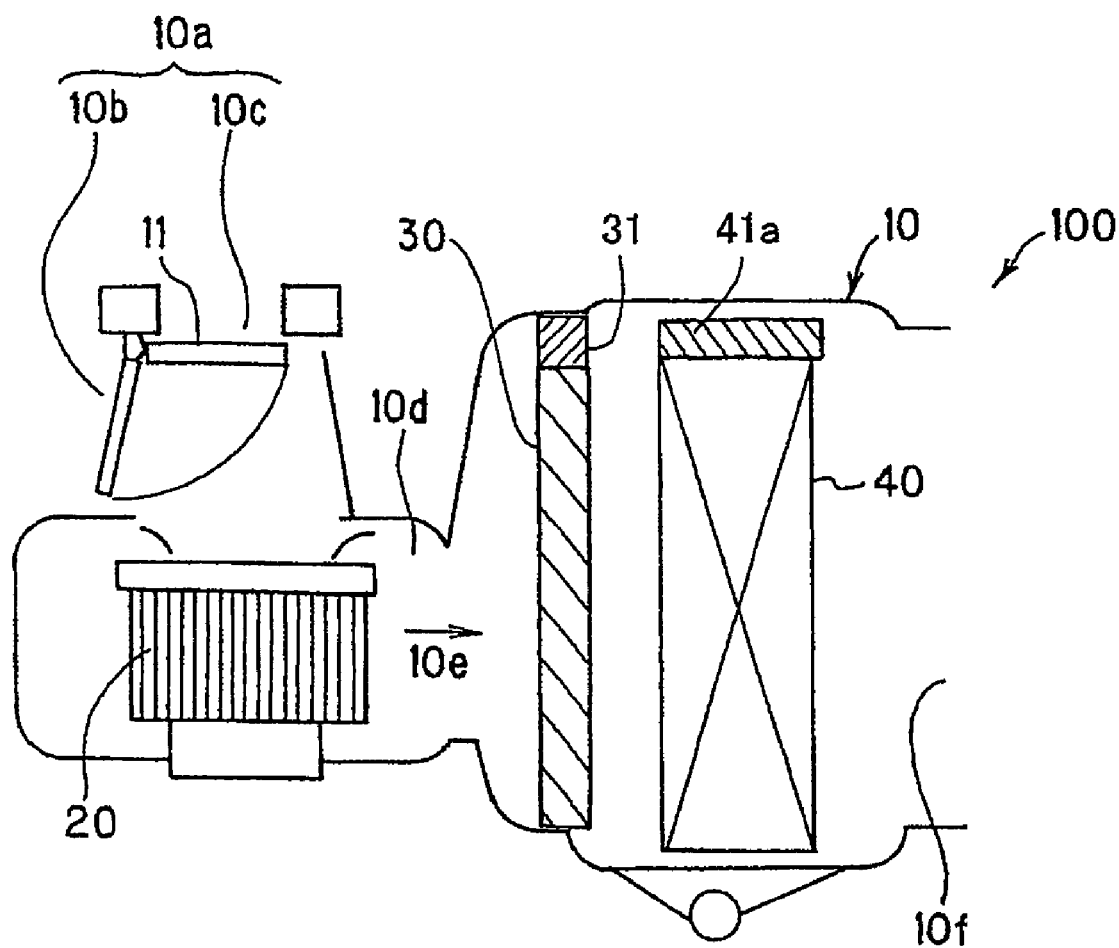
FIG. 3 is a side surface schematic diagram of a second embodiment of the air conditioner pertaining to this embodiment.
Figure 4:
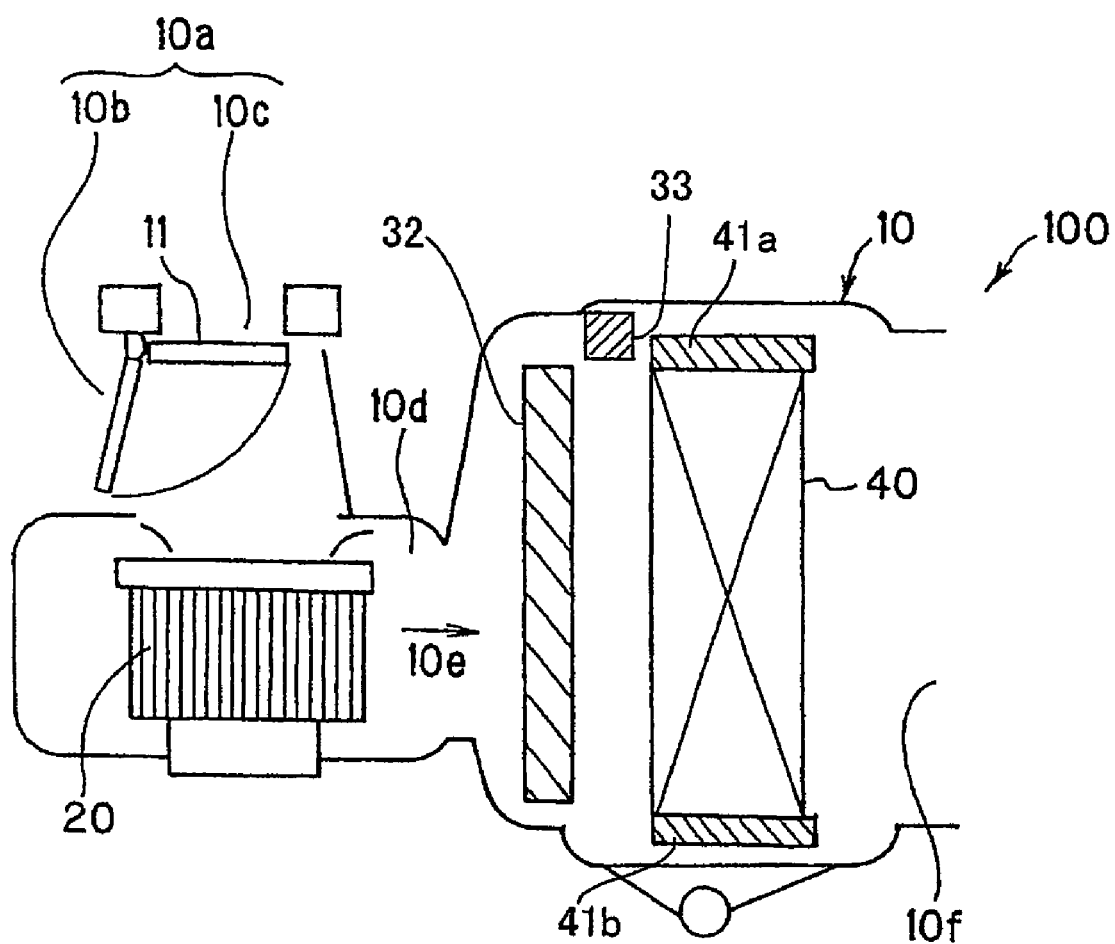
FIG. 4 is a side surface schematic diagram of a third embodiment of the air conditioner pertaining to this embodiment.

It is preferable that the thickness of the wall of the above-mentioned case on the downstream airflow side be formed thinner than the thickness of the wall on the upstream airflow side. FIG. 2 (a) is a type diagram of the filter unit of FIG. 1. An antibacterial agent case 31 is detachably fixed to the upper end surface of a filter frame 50 of the filter unit. FIG. 2 (b) is a schematic diagram of a cross section A-A' of the antibacterial agent case 31. In FIG. 2 (a), the filter unit 30, together with a dust-collecting filter 51 and odour-removing filter (not shown in the diagram), is assembled in a folded pleat shape in the filter frame 50 in which the filter end part is fixed in such a way as to not cover the filter surface. The UV-ray generating lamp has been omitted from the diagram. As is shown in FIG. 2(b), the thickness of the wall on the downstream airflow side of the antibacterial agent case 31 is formed thinner than the thickness of the wall of the upstream airflow side. When the airflow strikes the wall of the upstream airflow side, the gas-permeated the antibacterial agent is spattered and lost from the wall surface at an early stage. As diffusion of the permeated gas occurs in response to the concentration gradient, if the antibacterial agent adsorbed on the wall surface comes off at an early stage during gas permeation the antibacterial agent concentration on the wall surface will be reduced and gas permeation of the antibacterial agent will be quickened. The suppression of microorganism propagation in the evaporator and the environs thereof is better when the antibacterial agent is slowly disseminated in a state in which there is no airflow in the air passage when the air-conditioner is stopped rather than when the air conditioner is operating. Accordingly, it is desirable that the antibacterial agent case possess the characteristic of preventing the quickening of the gas permeation of the antibacterial agent that is caused by a received flow of airflow and, furthermore, that it be arranged in a position that does not obstruct the airflow. As is shown in the cross-section of FIG. 2(*b*), when the wall on the upstream side is made thicker, this wall is set to a thickness at which, even if the gas permeation of the antibacterial agent 52 is markedly reduced and a received flow of airflow occurs, the effects thereof are minimal. By way of example, the thickness of the wall is set to 1.6 to 3.0 mm or, more preferably, 1.8 to 2.2 mm. On the other hand, the volatilization of the antibacterial agent 52 due to exposure to the airflow will not occur when the thickness of the wall on the downstream side of the case which is unlikely to be exposed to an airflow is made thinner and, due to the thinning of the wall, the antibacterial agent 52 can be slowly disseminated with directionality to the evaporator side. It should be noted that the wall on the upstream side of the case is set to a thickness so that, when the temperature within the airflow passageway reaches a temperature of the order of 50° C., unnecessary gas permeation of the antibacterial agent 52 will not occur. By way of example, the thickness of the wall is set to 0.4 to 1.2 mm or, more preferably, 0.6 to 1.0 mm. The thickness of the wall of the lower wall and the upper wall of the antibacterial agent case shown in FIG. 2(*b*) is preferably set to a thickness that is between that of the thickness of the wall on the upstream side and that of the thickness of the wall on the downstream side.

Any type of antibacterial agent, provided it is an antibacterial agent that volatilizes at room temperature, can be used. Examples thereof include hinokithiol, cinnamon aldehyde and isothiocyanates and so on although allyl isothiocyanate is particularly preferred for its antibacterial characteristics at low concentration and its gas-permeable property through synthetic polymers. In this embodiment mode the allyl isothiocyanate is adsorbed on a porous body medium such as zeolite or impregnated in a medium such as a water-absorbing polymer, and this medium is sealed in the synthetic polymer case. An example of a preferred material for the case material is polypropylene that, by a process of diffused osmosis, is gas-permeable by allyl isothiocyanate. A lid, without a ventilation hole, is fitted perfectly on the case by ultrasonic welding. The allyl isothiocyanate disseminates slowly to gas-permeate the wall of the polypropylene case.

In this embodiment mode it is preferable that the case 31 be juxtaposedly arranged with the upper part tank part 41*a* and, as shown in FIG. 1, it is even more preferable that the case 31 be juxtaposedly arranged in the upper part tank part 41*a* in such a way that the case 31 does not project from the upper tank part 41*a* with respect to the direction of airflow. By the juxtaposition of the case in this way, no increase in obstruction to the airflow occurs and unnecessary volatilization of the antibacterial agent is suppressed.

The evaporator of the air conditioner of this embodiment may be either a single tank-type in which the tank part is provided on one end part or a dual tank type in which tank parts are provided in both end parts. FIG. 1 shows the case of a dual tank-type evaporator in which the upper tank part 41*a* is provided in the upper end part of the evaporator and a lower tank part 41*b* is provided in the lower end part thereof. A fin (not shown in the diagram) is arranged in the centre part of the evaporator to raise the efficiency of heat exchange between the tube element through which the refrigerant passes, the airflow and the refrigerant. As shown in FIG. 3, which shows a second embodiment of the air conditioner, a single tank-type evaporator may be provided instead of a dual tank-type evaporator.

Although FIG. 1 shows a mode in which the case 31 is detachably fixed to the upper end surface of the frame of a filter 30 arranged in the upstream airflow side of the evaporator 40, as shown in FIG. 4, which shows a third embodiment of the air conditioner, a case 33 may be fixed to the air conditioner main body 10 in which the air passageway is formed. In this case, it is preferable that the case be juxtaposedly arranged with the tank part 41a in such a way that it causes no obstruction to the airflow.

Figure 5:
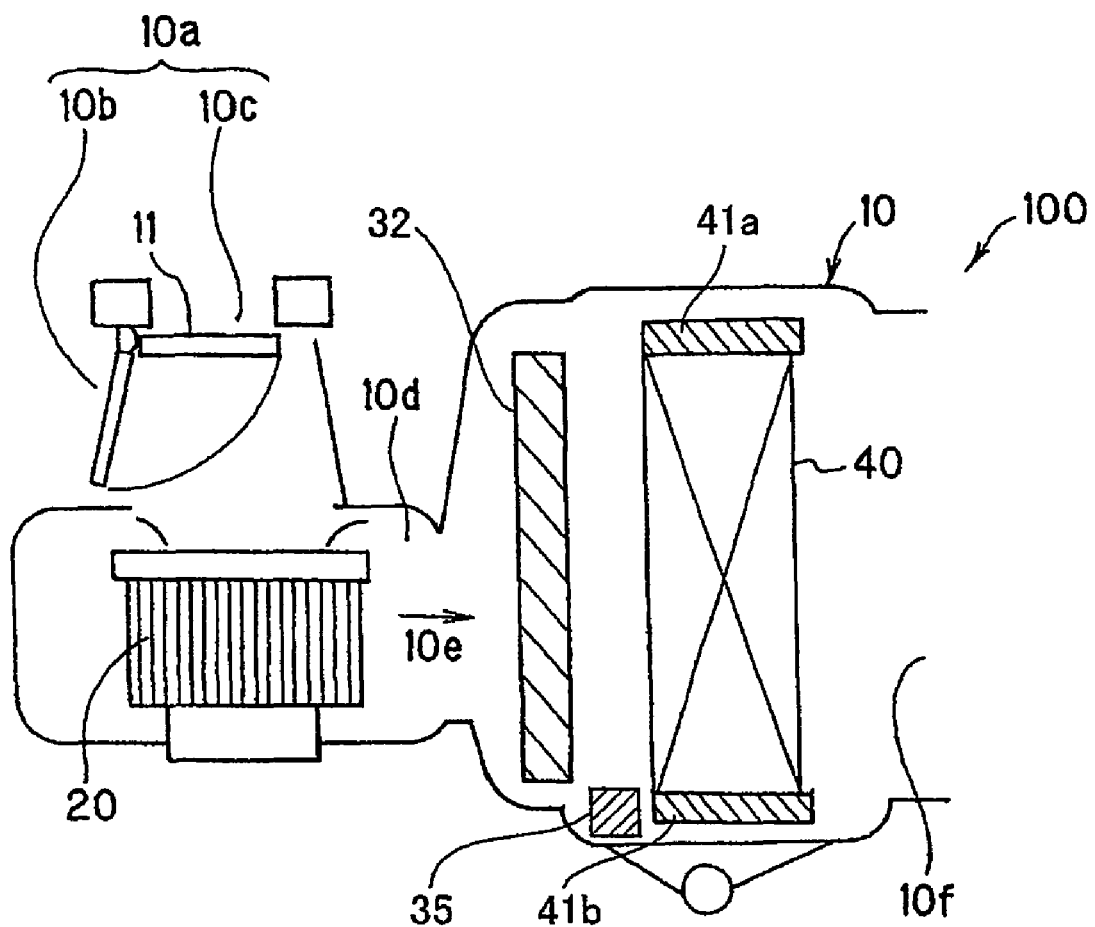
FIG. 5 is a side surface schematic diagram of a fourth embodiment of the air conditioner pertaining to this embodiment.

It should be noted that, as in FIG. 5, which shows a fourth embodiment of the air conditioner, a case 35 may be juxtaposedly arranged in the lower part tank part 41b of a dual tank-type evaporator.

If an adhesive is affixed to the upper wall or lower wall of the case, it is preferable that the wall of the adhesion surface of the case be formed thicker. This is because there is a fear that, when osmosis of antibacterial agent through the adhesion surface occurs, the adhesion strength thereof will be lowered. By way of example, the thickness of this wall is formed to be greater than 3 mm.

Figure 6:
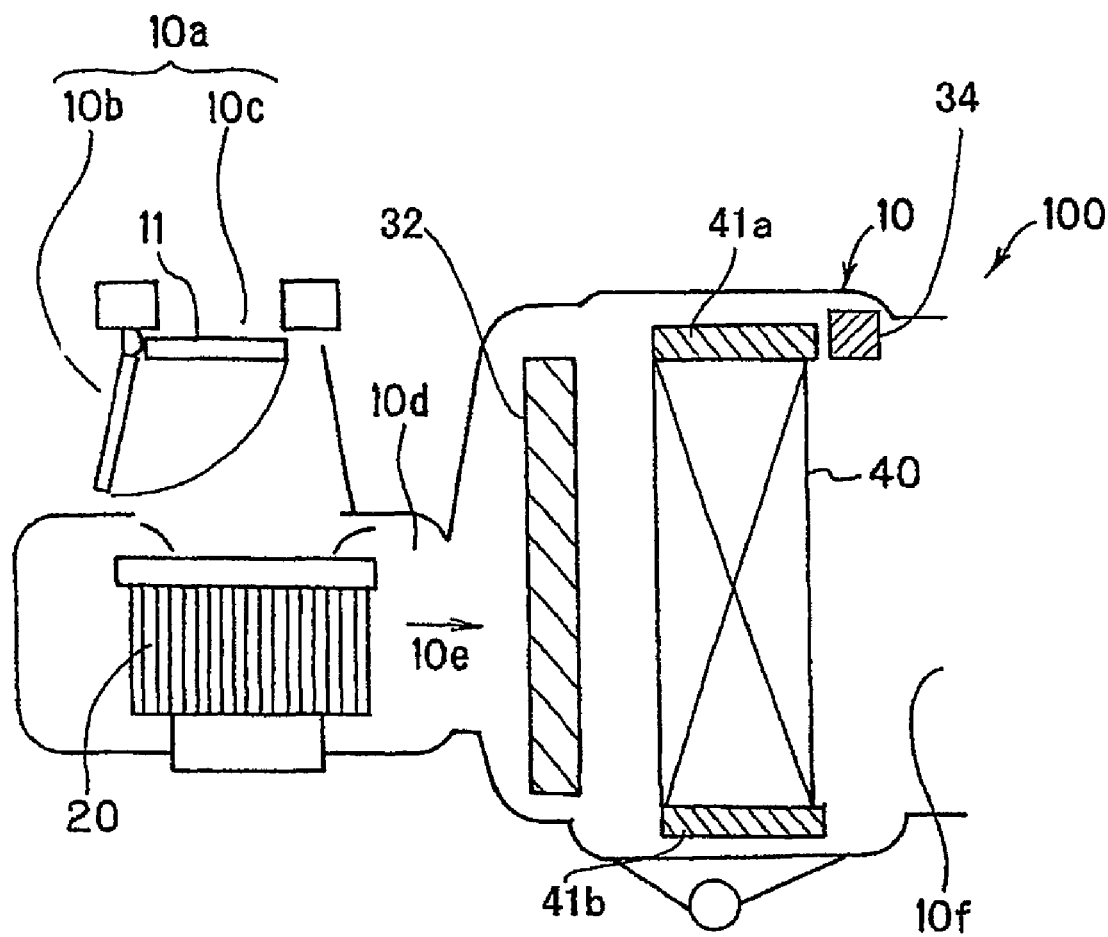
FIG. 6 is a side surface schematic diagram of a fifth embodiment of the air conditioner pertaining to this embodiment.
Figure 7:
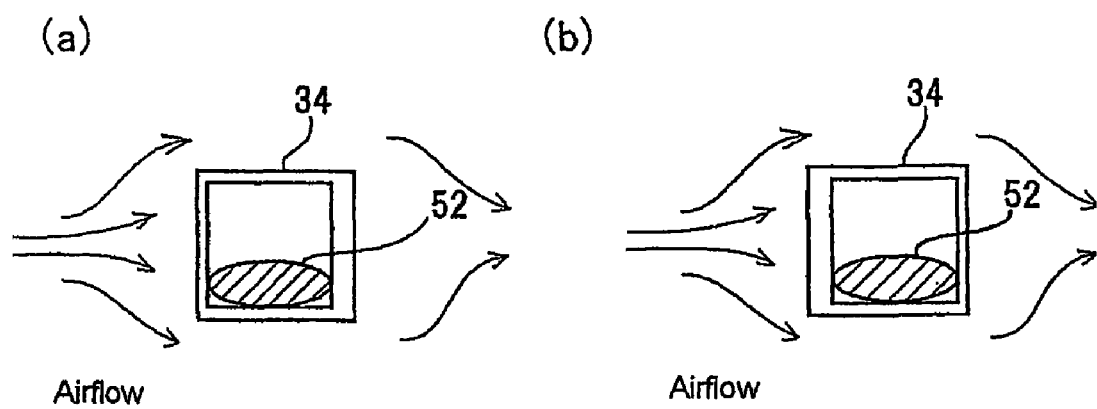
FIG. 7 is a schematic type diagram of the horizontal cross-section of the case of the fifth embodiment of the air conditioner pertaining to this embodiment, wherein (a) shows a case in which the thickness of the wall on the evaporator side is formed thinner than the thickness of the wall on the downstream airflow side, and (b) shows the case in which the wall of the case on the upstream airflow side is formed thicker and the wall of the case on the downstream side is formed thinner.

A fifth embodiment of the air conditioner is shown in FIG. 6. As shown in. FIG. 6, when a case 34 is arranged in the downstream side of the evaporator 40, it is conditional that the case 34 be juxtaposedly arranged with the tank part 41a and, more preferably, it is conditional that the case 34 be juxtaposedly arranged in such a way that is does not project from the tank part 41a with respect to the direction of airflow and, as is shown in FIG. 7(a), in the case 34, which is formed of a thickness that allows gas permeation of the antibacterial agent, the thickness of the wall on the evaporator side may be formed thinner that the thickness of the wall on the airflow downstream side. That is to say, as shown in FIG. 7 (b), although it is preferable that the wall of the case on the airflow upstream side be formed thicker and the wall of the case on the downstream side be formed thinner, where the case 34 is juxtaposedly arranged in the tank part 41a with respect to the direction of airflow, almost none of the airflow strikes the case 34. Accordingly, as shown in FIG. 7 (a), even if the thickness of the wall on the evaporator side is formed thinner, no unnecessary volatilization of the antibacterial agent cause by airflow occurs. On the other hand, provided the antibacterial agent is slowly disseminated to the evaporator, the suppression effect on microorganism propagation will be increased.

The antibacterial agent case 31 pertaining to this embodiment may be formed by the assembly of a plurality of small cases 31a, 31b that are able to be fixedly attached to each other as shown in FIG. 2 (a). These individual cases are hermetically sealed. By virtue of the fact that partition into small cases in this way is possible, adaptation to any size filter frame is possible by simply adjusting the number of cases that are to be fixed.

By virtue of the fact that, using the present invention as described above, the antibacterial agent is disseminated slowly in the required direction only, the lifespan of the antibacterial agent can be increased.

Figure 8:
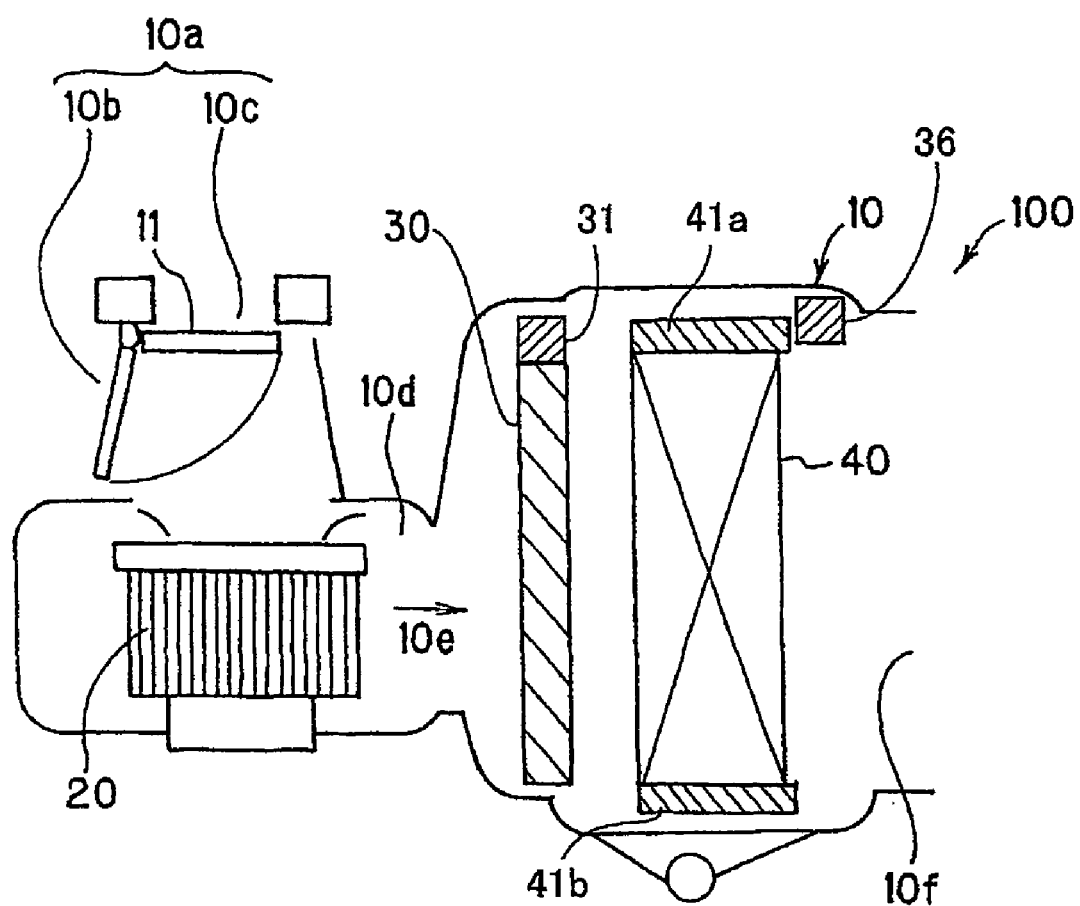
FIG. 8 is a side surface schematic diagram of a sixth embodiment of the air conditioner pertaining to this embodiment.

In this embodiment mode, as shown in the sixth embodiment as shown in FIG. 8, the cases 31, 36 may be arranged in both the front and rear of the evaporator 40. Where the case is juxtaposedly arranged to the side of the tank 41a as in the case 36 as shown in FIG. 8, the thickness of the wall on the evaporator side, as is shown in FIG. 7(a), may be formed thinner than the thickness of the wall on the downstream airflow side or, as shown in (b), the wall of the case on the upstream airflow side may be formed thicker and the wall of the case on the downstream airflow side may be formed thinner.

Employing a square antibacterial agent case in the air conditioner as shown in FIG. 1, volatilization tests of the antibacterial agent were carried out. The cross-sectional structure of the case of this embodiment is as shown in FIG. 2 (b), that is, the thickness of the wall on the upstream airflow side of the case is 2 mm and the thickness of the wall on the downstream airflow side the case is 0.8 mm. In addition, as a comparative embodiment, a case in which the thickness of all walls was 1.0 mm was employed. The level of volatilized antibacterial agent generated from the case and the concentration (40° C.) of the antibacterial agent in an HVAC were measured. The level of volatilization was obtained from a measurement of weight reduction of the case when placed in a 40° C. environment. The concentration of the antibacterial agent within the HVAC was measured 1 hour following the stoppage of the operation of the blower under a condition of, employing a wind tunnel, air conditioner temperature 40° C. The results thereof are shown in Table 1.

TABLE 1

| The type of the case | The thickness of the wall | The level of volatilized antibacterial agent (40° C.) | The concentration of the antibacterial agent in the HVAC (40° C.) |
|---|---|---|---|
| this embodiment | 0.8 mm (on the downstream airflow side) 2.0 mm (on the upstream airflow side) | 30 mg/day | 10 ppm |
| comparative embodiment | 1.0 mm (all walls) | 40 mg/day | 10 ppm |

Despite the fact that, in the embodiment, the level of volatilization of the antibacterial agent was smaller, the concentration of the antibacterial agent within the HVAC was the same as that of the comparative embodiment. Accordingly, the lifespan of the antibacterial agent was longer.

The invention claimed is:

1. An air conditioner that comprises, in an air passageway through which an airflow from an air intake port towards a clean air discharge port is formed, at the least, an air blower for generating airflow, an evaporator and, arranged in the upstream airflow side and/or downstream airflow side of said evaporator, a synthetic polymer case in which an antibacterial agent impregnated in a medium such as a porous body or water-absorbing polymer is sealed, which air conditioner is characterized in that a thickness of a wall on the downstream airflow side of the synthetic polymer case is formed thinner than a thickness of a wall of the upstream airflow side, and in that the wall on the downstream airflow side is formed to allow gas permeation of the antibacterial agent.

2. An air conditioner according to claim 1, characterized in that the evaporator is a single tank-type in which the tank part is provided in one end, or is a double tank-type in which tank parts are provided in both ends, wherein the synthetic polymer case is juxtaposedly arranged with the tank part.

3. An air conditioner according to claim 2, characterized in that the synthetic polymer case does not project from the tank part with respect to the direction of airflow.

4. An air conditioner according to claims 1, 2 or 3, characterized in that the synthetic polymer case is detachably fixed to a filter frame arranged in the upstream airflow side of the evaporator.

5. An air conditioner that comprises, in an air passageway through which an airflow from an air intake port towards a clean air discharge port is formed, at the least, an air blower for generating airflow, an evaporator of a single tank-type in which a tank is provided in one end or a double tank-type in which tank parts are provided in both ends and, arranged in the upstream airflow side and/or downstream airflow side of said evaporator, a synthetic polymer case in which an antibacterial agent impregnated in a medium such as a porous body or water-absorbing polymer is sealed, which air conditioner is characterized in that a thickness of a wall on the downstream airflow side of the synthetic polymer case is formed thinner than a thickness of a wall of the upstream airflow side, and in that the wall on the downstream airflow side is formed to allow gas permeation of the antibacterial agent.

6. An air conditioner according to claim 5, characterized in that the synthetic polymer case does not project from the tank part with respect to the direction of airflow.

7. An air conditioner according to claim 5, characterized in that the synthetic polymer case is formed from polypropylene, and in that the antibacterial agent is allyl isothiocyanate.

8. An air conditioner according to claim 5, characterized in that the synthetic polymer case is formed by the assembly of a plurality of small cases detachably fixed to each other.

9. An air conditioner according to claim 1, characterized in that the synthetic polymer case is formed from polypropylene, and in that the antibacterial agent is allyl isothiocyanate.

10. An air conditioner according to claim 1 characterized in that the synthetic polymer case is formed by the assembly of a plurality of small cases detachably fixed to each other.

* * * * *